(12) United States Patent
Baguley et al.

(10) Patent No.: US 7,510,830 B2
(45) Date of Patent: Mar. 31, 2009

(54) CANCER TREATMENT BY COMBINATION THERAPY

(75) Inventors: Bruce Charles Baguley, Auckland (NZ); Lai-Ming Ching, Auckland (NZ); Martin Philpott, Auckland (NZ)

(73) Assignee: Cancer Research Technology Limited, London (GB)

( * ) Notice: Subject to any disclaimer, the term of this patent is extended or adjusted under 35 U.S.C. 154(b) by 699 days.

(21) Appl. No.: 10/341,736

(22) Filed: Jan. 14, 2003

(65) Prior Publication Data

US 2004/0087611 A1    May 6, 2004

Related U.S. Application Data

(63) Continuation of application No. PCT/NZ01/00154, filed on Jul. 27, 2001.

(30) Foreign Application Priority Data

Jul. 28, 2000    (NZ) ...................... 506060

(51) Int. Cl.
*A61K 39/395* (2006.01)
*A61K 38/00* (2006.01)

(52) U.S. Cl. .................. 435/6; 424/145.1; 514/285; 514/453; 514/455

(58) Field of Classification Search .......... 514/285, 514/453, 455; 424/145.1
See application file for complete search history.

(56) References Cited

U.S. PATENT DOCUMENTS

| 3,678,077 A | 7/1972 | Nakanishi et al. |
| 4,602,034 A | 7/1986 | Briet et al. |
| 4,704,355 A | 11/1987 | Bernstein |
| 5,126,129 A | 6/1992 | Wiltrout et al. |
| 5,281,620 A | 1/1994 | Denny et al. ................. 514/455 |
| 5,464,826 A | 11/1995 | Grindey et al. |
| 5,620,875 A | 4/1997 | Hoffman et al. ............. 435/123 |
| 5,817,684 A | 10/1998 | Fleisch et al. ................ 514/381 |
| 5,863,904 A | 1/1999 | Nabel et al. .................... 514/44 |
| 5,910,505 A | 6/1999 | Fleisch et al. ................ 514/381 |
| 5,914,340 A | 6/1999 | Fleisch et al. ................ 514/381 |
| 5,977,077 A | 11/1999 | Winter et al. ................. 514/23 |
| 5,998,454 A | 12/1999 | Fleisch et al. ................ 514/381 |
| 6,174,873 B1 | 1/2001 | Wrenn |
| 6,194,454 B1 | 2/2001 | Dow |
| 6,806,257 B1 | 10/2004 | Lee et al. |
| 2001/0027210 A1 | 10/2001 | Wilson ........................ 514/455 |
| 2001/0041713 A1 | 11/2001 | Waldstreicher et al. |
| 2003/0003092 A1 | 1/2003 | Krissansen et al. |
| 2004/0204480 A1 | 10/2004 | Wilson et al. |
| 2005/0131059 A1 | 6/2005 | Wang et al. |
| 2006/0009505 A1 | 1/2006 | Baguley et al. |
| 2007/0060637 A1 | 3/2007 | Wilson et al. |
| 2007/0082937 A1 | 4/2007 | Baguley et al. |
| 2008/0070847 A1 | 3/2008 | Wilson et al. |
| 2008/0070848 A1 | 3/2008 | Wilson et al. |
| 2008/0070849 A1 | 3/2008 | Wilson et al. |
| 2008/0070886 A1 | 3/2008 | Wilson et al. |

FOREIGN PATENT DOCUMENTS

| DE | 2015265 A1 | 10/1970 |
| DE | 19721211 A1 | 11/1998 |
| EP | 0278176 | 8/1988 |
| EP | 0326149 A2 | 8/1989 |
| EP | 0385467 A | 9/1990 |
| EP | 0488718 A2 | 6/1992 |
| EP | 0 584 001 A1 | 7/1993 |
| EP | 0551200 A1 * | 7/1993 |
| EP | 0551200 A1 * | 7/1993 |
| EP | 0 743 064 | 11/1996 |
| EP | 0 584 001 B1 | 5/1997 |
| GB | 0121285.1 | 9/2001 |
| GB | 0206839.3 | 5/2002 |
| GB | 0225508.1 | 11/2002 |
| GB | 0604114.9 | 3/2006 |
| GB | 0157387.7 | 8/2006 |
| GB | 0517386.9 | 8/2006 |
| JP | 2001247459 | 9/2001 |
| NZ | 336259 | 6/1999 |
| NZ | 506060 | 7/2000 |
| WO | WO 98/25600 | 6/1988 |
| WO | WO 91/04014 | 4/1991 |
| WO | WO 94/23753 | 10/1994 |
| WO | WO 95/09621 | 4/1995 |
| WO | WO 9632418 A1 * | 10/1996 |
| WO | WO 96/36347 A1 | 11/1996 |

(Continued)

OTHER PUBLICATIONS

Economou et al. (Immunology 1989, 67:514-519).*

(Continued)

*Primary Examiner*—Brandon J Fetterolf
(74) *Attorney, Agent, or Firm*—Foley & Lardner LLP

(57) ABSTRACT

Methods and compositions are provided for treating cancer, the methods including the step administering, either sequentially or simultaneously, (i) a compound of the xanthenone acetic acid group of compounds, and (ii) at least one compound selected from compounds which modulate TNF production and compounds which act on biochemical pathways leading to TNF synthesis. Compositions include a combination of (i) and (ii) above, together with acceptable pharmaceutical carriers and/or vehicles.

12 Claims, 8 Drawing Sheets

FOREIGN PATENT DOCUMENTS

| WO | WO 9704761 A1 * | 2/1997 |
|---|---|---|
| WO | WO 97/34482 | 9/1997 |
| WO | WO 98/25615 A1 | 6/1998 |
| WO | WO 98/25616 A1 | 6/1998 |
| WO | WO 98/42332 | 10/1998 |
| WO | WO 98/42334 A1 | 10/1998 |
| WO | WO 98/42335 | 10/1998 |
| WO | WO 98/42336 | 10/1998 |
| WO | WO 98/42337 | 10/1998 |
| WO | WO 98/42345 A1 | 10/1998 |
| WO | WO 98/42346 | 10/1998 |
| WO | WO 98/42650 | 10/1998 |
| WO | WO 00/10600 A2 | 3/2000 |
| WO | WO 00/10600 A3 | 3/2000 |
| WO | WO 00/16798 | 3/2000 |
| WO | WO 00/48591 | 8/2000 |
| WO | WO 01/34135 A2 | 5/2001 |
| WO | WO 01/34137 A2 | 5/2001 |
| WO | WO 01/34197 A2 | 5/2001 |
| WO | WO 01/34198 A2 | 5/2001 |
| WO | WO 02/09700 A1 | 2/2002 |
| WO | WO 03/020259 A2 | 3/2003 |
| WO | WO 03/080044 | 10/2003 |
| WO | WO 2004/039363 | 5/2004 |
| WO | WO 2005/027974 A1 | 3/2005 |
| WO | WO 2007/023302 | 3/2007 |
| WO | WO 2007/023307 | 3/2007 |

OTHER PUBLICATIONS

Philpott et al. (IDS, Cancer Chemother. Pharmacol. 1995; 36: 143-148).*
Joseph et al. (Cancer Research 1999; 59: 633-638).*
Wiesenthal (http://weisenthal.org/feedback.html, Feb. 4, 2002).*
Maier et al. (Anti-Cancer Drugs 1997; 8: 238-244).*
Holmes (Seminars in Oncology 1996; 23: 46-56).*
Philpott et al. (Cancer Chemother. Pharmacol. 1995; 36: 143-148).*
Rieckmann et al. (Biochem. Biophys. Res. Commun. 1992; 1857: 51-57).*
Nakamura et al. (Jpn. J. Cancer Research (Gann) 1986; 77: 767-773).*
Wilson, W., Baguley B.; "Combination of the Antivascular Agent DMXAA with Radiation and Chemotherapy", *International Journal of Oncology, Biology and Physics*, vol. 46, No. 3, Feb. 1, 2000, abstract 46, p. 706.
Rustin, G.; "Vascular Targeting in the Clinic"; Abstract; *ICTR 2000: 1st Int'l Conference on Translational Research A.*, 2000.
Baguley, B.C. et al; "291 Mechanisms of Tumor Blood Flow Inhibition by The Antitumour Drug DMXAA (5,6-dimethylxanthenone-4-acetic acid"; *Proceedings of the 11th NCI EORTC AACR Symposium; Copyright © 2000 Stichting NCI-EORTC Symposium on new drugs in cancer therapy; publ. By the AACR*; Published as a Supplement to Clinical Cancer Research, vol. 6, Nov. 2000.
Chaplin, D.J., et al; "Antivascular approaches to solid therapy; evaluation of tubulin binding agents"; *Proc. Annu. Meet. Am. Assoc. Cancer Res.*, Mar. 1996, vol. 37, #3009: 440-441 and Abstract.
Hornung R. L., et al; "Augmentation of Natural Killer Activity, Induction of IFN and Development Tumor Immunity During the Successful Treatment of Established Murine Renal Cancer Using Flavone Acetic Acid and IL-2"; *The Journal of Immunology* (1988) vol. 141(10), pp. 3671-3679.
Thomsen, L.L., et al.; "Nitric Oxide Production in endotoxin-resistant C3H/HeJ mice stimulated with flavone-8-acetic acid and xanthenone-4-acetic acid analogues"; *Biochem. Pharmacol*, 43(11); pp. 2401-2406; 1992.
Lash, C.J., et al.; "Enhancement of the anti-tumor effects of the antivascular agent 5,6-dimethylxanthenone-4-acetic acid (DMXAA) by combination with 5-hydroxytryptamine and bioreductive drugs"; *Br. J. Cancer*, 78(4), pp. 439-445, 1998.

Pedley, R.B., et al.; "Enhancement of antibody-directed enzyme prodrug therapy in colorectal xenografts by an antivascular agent"; *Cancer Res.*, 59(16), pp. 3998-4003, Aug. 15, 1999.
Pruijn, F.B., et al.; "Mechanisms of enhancement of the antitumor activity of melphalan by the tumor blood flow inhibitor 5,6-dimethylxanthenoone-4-acetic acid"; *Cancer Chemother. Pharmacol.*, 39(6), pp. 541-546, 1997.
Rewcastle, et al.; "Potential Antitumor Agents. 58. Synthesis and Structure-Activity Relationships of Substituted Xanthenone-4-acetic Acids Active against the Colon 38 Tumor in Vivo"; *J. Med. Chem.* 32(4), pp. 793-799, 1989.
Cliffe, S., et al.; "Combining bioreductive drugs (SR 4233 or SN 23862) with the vasoactive agents flavone acetic acid or 5,6-dimethylxanthenone acetic acid"; *Int. J. Radiation Oncology Biol. Phys.*, 29(2), pp. 373-377, 1994.
Phillips, R.M. "Inhibition of DT-diaphorase (NAD(P)H:quinone oxidoreductase, EC 1.6.99.2) by 5, 6-dimethylxanthenone-4-acetic acid (DMXAA) and flavone-8-acetic acid (FAA): implications for bioreductive drug development"; *Biochem. Pharmacol.*, 58(2), pp. 303-310, 1999.
Ching, L.-M., et al.; "Effect of thalidomide on tumor necrosis factor production and anti-tumor activity induced by 5, 6-dimethylxanthenone-4-acetic acid"; *Br. J. Cancer*, 72(2), pp. 339-343, 1995.
Brown, W.L., et al.; "Suppression of serum tumor necrosis factor-α by thalidomide does not lead to reversal of tumor vascular collapse and anti-tumor activity of 5, 6-dimethylxanthenone-4-acetic acid"; *Anticancer Res.*, 18(6A), pp. 4409-4414, 1998.
Ching, L.M., et al.; "Interaction of thalidomide, phthalimide analogues of thalidomide and pentoxifylline with the antitumor agent 5, 6-dimethylxanthenone-4-acetic acid: concomitant reduction of serum tumor necrosis factor-alpha and enhancement of antitumor activity"; *Br. J. Cancer.*, 78(3), pp. 336-343, 1998.
Kestell, P., et al.; "Modulation of the pharmacokinetics of the antitumor agent 5,6-dimethylxanthenone-4-acetic acid (DMXAA) in mice by thalidomide"; *Cancer Chemother. Pharmacol.*, 46(2), pp. 135-141, 2000.
Cao, Z., et al.; "Thalidomide increases both intra-tumoural tumor necrosis factor-alpha production and anti-tumor activity in response to 5, 6-dimethylxanthenone-4-acetic acid"; *Br. J. Cancer*, 80(5/6), pp. 716-723, 1999.
Baguley, B.C., et al.; "Serotonin involvement in the antitumour and host effects of flavone-8-acetic acid and 5, 6-dimethylxanthenone-4-acetic acid"; *Cancer Chemother. Pharmacol.*, 33(1), pp. 77-81, 1993.
Zai, L.J., et al.; "Correlation between immune and vascular activities of xanthenone acetic acid antitumor agents"; *Oncol. Res.*, 6(2), pp. 79-85, 1994.
Zhao, L., et al.; "Effects of the serotonin receptor antagonist cyproheptadine on the activity and pharmacokinetics of 5, 6-dimethylxanthenone-4-acetic acid (DMXAA)"; *Cancer Chemother. Pharmacol.*, 47(6), pp. 491-497, 2001.
Futami, H., et al.; "Cytokine induction and therapeutic synergy with interleukin-2 against murine renal and colon cancers by xanthenone-4-acetic acid derivatives"; *J. Immunother.*, 12(4), pp. 247-255, 1992.
Ching, L.M., et al.; "Interaction between endotoxin and the antitumour agent 5, 6-dimethylxanthenone-4-acetic acid in the induction of tumor necrosis factor and haemorrhagic necrosis of colon 38 tumors"; *Cancer Chemother. Pharmacol.*, 35(2), pp. 153-160, 1994.
Ching, L.M., et al.; "Induction of intratumoral tumor necrosis factor (TNF) synthesis and hemorrhagic necrosis by 5, 6-dimethylxanthenone-4-acetic acid (DMXAA) in TNF knockout mice"; *Cancer Res.*, 59(14), pp. 3304-3307, 1999.
Thomsen, L.L., et al.; "Tumor-dependent increased plasma nitrate concentrations as an indication of the antitumor effect of flavone-8-acetic acid and analogues in mice"; *Cancer Res.*, 51(1), pp. 77-81, 1991.
Baguley, et al.; "Evidence that the 5-hydroxytryptamine antagonist, cyproheptadine, modulates nitric oxide production in mice in response to flavone acetic acid, vinblastine and other agents"; *Biol. Nitric Oxide, Proc. Int. Mett.*; Meeting Date 1991, vol. 2, (1992); 222-224, 1991.

Kanwar, J.R., et al.; "Taking lessons from dendritic cells: Multiple xenogeneic ligands for leukocyte integrins have the potential to stimulate anti-tumor immunity"; *Gene Therapy*, 6: pp. 1835-1844, 1999.

Kanwar, J.R., et al.; "Vascular attack by 5, 6-dimethylxanthenone-4-acetic acid combined with B7.1-mediated immunotherapy overcomes immune-resistance and leads to the eradication of large tumors"; *Cancer Res.*, 61(5), pp. 1948-1956, 2001.

Fujii H, et al, "Vacccination with B7-1 tumor and anti-adhesion therapy with RGD pseudo-peptide (FC-336) efficiently induce anti-metastatic effect"; *Clinical & Experimental Metastasis*, vol. 16, pp. 141-148, 1998.

Zitvogel L., et al.; "Interleukin-12 and b7.1 co-stimulation co-operate in the induction of effective antitumor immunity and therapy of established tumor"; *Eur. J. Immunol*, (1996), vol. 26, pp. 1335-1341.

Lissoni P., et al, "Neuroimmunotherapy of advanced solid neoplasms with single evening subcutaneous injection of low-dose interleukin-2 and melatonin Preliminary results"; *European Journal of Cancer*, (1993), vol. 29A(2), pp. 185-189.

Nawrocki S., and Mackiewicz A., "Genetically modified tumor vaccines-where we are today"; *Cancer Treatment Reviews*, (1999), vol. 25, pp. 29-46.

Thrash-Bingham C. A., and Tartof K. D.; "aHIF: A natural antisense transcript overexpressed in human renal cancer during hypoxia"; *The Journal of the National Cancer Institute*, (1999), vol. 91(2), pp. 143-151.

"Combretastatin Update 1: In Ohio Phase 1 Trial, Some Tumors Respond, Patients Experience Vascular Stress"; *PSA Rising; Medical Pike Briefs; Headline Index: Clinical Trial Phase 1 Results*; Nov. 8, 1999.

Zhou, et al.; "A difference between the rat and mouse in the pharmacokinetic interaction of 5, 6-dimethylxanthenone-4-acetic acid with thalidomide"; *Cancer Chemother Pharmacol*, (2001), 47(6), 541-544.

Zhou, et al.; "Determination of unbound concentration of the novel anti-tumor agent 5, 6-dimethylxanthenone-4-acetic acid in human plasma by ultrafilteration followed by high-performance liquid chromatography with fluorimetric detection"; *J. of Chromatography B*; (2001) 757(2), 359-363.

Zhou, et al.; "Determination of the covalent adducts of the novel anti-cancer agent 5, 6-dimethylxanthenone-4-acetic acid in biological samples by high-performance liquid chromatography"; *J. of Chromatography B;* (2001) 757: 343-348.

Zhou, et al.; "Reversible binding of the novel anti-tumor agent 5, 6-dimethylxanthenone-4-acetic acid to plasma proteins and its distribution into blood cells in various species"; *J. of Pharmacy and Pharmacology*; (2001) 53(4), 463-471.

Zhou, et al.; "In vitro and in vivo kinetic interactions of the antitumour agent 5, 6-dimethylxanthenone-4-acetic acid with thalidomide and diclofenac"; *Cancer Chemother. Pharmacol.*; (2001) 47(4), 319-326.

Cao, et al; "Interferon-inducible Protein 10 Induction and Inhibition of Angiogenesis in Vivo by the Antitumor Agent 5, 6-Dimethylxanthenone-4-acetic Acid (DMXAA)"; *Cancer Research*; (2001) 61(4), 1517-1521.

Zhou, et al.; "Identification of the Human Liver Cytochrome P450 Isoenzyme Responsible for the 6-Methylhydroxylation of the Novel Anticancer Drug 5, 6-Dimethylxanthenone-4-Acetic Acid"; *Drug Metabolism and Disposition, A Publication of The American Soc. for Pharma. and Exper. Therap.*; (2000) 28(12) 1449-1456.

Siim, et al.; "Scintigraphic Imaging of the Hypoxia Marker $^{99m}$Technetium-labeled 2,2'(1,4-Diaminobutane) bis (2-methyl-3-butanone) Dioxime ($^{99m}$Tc-labeled HL-91; Prognox): Noninvasive Detection of Tumor Response to the Antivascular Agent 5, 6-Dimethylxanthenone-4-acetic Acid"; *Cancer Research*; (2000) 60(16), 4582-4588.

Aitken, et al.; "Synthesis and Antitumour Activity of New Derivatives of Flavone-8-acetic Acid (FAA), Part 4: Variation of the Basic Structure"; *Arch. Pharm. Pharm. Med. Chem.*; (2000) 333(6) 181-188.

Zhou, et al.; "Determination of two major metabolites of the novel anti-tumor agent 5, 6-dimethylxanthenone-4-acetic acid in hepatic microsomal incubations by high-performance liquid chromatography with fluorescence detection"; *J. of Chromatography B*; (1999) 734(1): 129-136.

Ching, et al.; "Induction of STAT and NFkB Activation by the Antitumor Agents 5,6-Dimethylxanthenone-4-acetic Acid and Flavone Acid in a Murine Macrophage Cell Line"; *Biochemical Pharmacology*; (1999) 58(7) 1173-1181.

Cao, et al.; "Thalidomide increases both intratumoural tumor necrosis factor-α production and anti-tumor activity in response to 5, 6-dimethylxanthenone-4-acetic acid"; *British Journal of Cancer*; (1999) 80(5,6), 716-723.

Kestell, et al.; "Plasma disposition, metabolism and excretion of the experimental antitumour agent 5, 6-dimethylxanthenone-4-acetic acid in the mouse, rat and rabbit"; *Cancer Chemother. Pharmacol.*; (1999) 43(4), 323-330.

Joseph, et al.; "Stimulation of Tumors to Synthesize Tumor Necrosis Factor-α in Situ Using 5,6-Dimethylxanthenone-4-acetic Acid: A Novel Approach to Cancer Therapy"; *Cancer Res.* (1999) 59(3), 633-638.

Wilson, et al.; "Enhancement of Tumor Radiation Response by the Antivascular Agent 5, 6-Dimethylxanthenone-4-Acetic Acid"; *Int. J. Radiation Oncology Biol. Phys.*; (1998) vol. 42 No. 4, 905-908.

Zaks-Zilberman, et al; "Induction of Adrenomedullin mRNA and Protein by Lipopolysaccharide and Paclitaxel (Taxol) in Murine Macrophages"; *Infection and Immunity*; (1998) 66 (10), 4669-4675.

Pang, et al.; "Antitumour Activity of the Novel Immune Modulator 5, 6-Dimethylxanthenone-4-acetic Acid (DMXAA) in Mice Lacking the Interferon-gamma Receptor"; *European Journal of Cancer*; (1998) 34(8): 1282-1289.

Siim, et al.; "Nitro Reduction as an Electronic Switch for Bioreductive Drug Activation"; *Oncology Research*; (1997) 9(6/7), 357-369.

Baguley, et al.; "Increased Plasma Serotonin Following Treatment With Flavone-8-Acetic Acid, 5,6-Dimethylxanthenone-4-Acetic Acid, Vinblastine, and Colchicine: Relation to Vascular Effects"; *Oncology Research*; (1997) 9(2), 55-60.

Moilanen, et al.; "Persistent induction of nitric oxide synthase in tumours from mice treated with the anti-tumor agent 5, 6-dimethylxanthenone-4-acetic acid"; *British Journal of Cancer*; (1998) 77(3): 426-433.

Philpott, et al.; "Production of tumor necrosis factor-α by cultured human peripheral blood leukocytes in response to the anti-tumor agent 5, 6-dimethylxanthenone-4-acetic acid (NSC 640488)"; *British Journal of Cancer*; (1997) 76(12): 1586-1591.

Everett, et al.; "High-performance ion chromatography applied to free-radical mechanisms in drug design. The problem of ion analysis at high ionic strengths"; *Journal of Chromatography A.*; (1997) 770(1,2), 273-279.

Patel, et al.; "The Effect of 5, 6-Dimethylxanthenone-4-acetic acid on Tumor Necrosis Factor Production by Human Immune Cells"; *Anticancer Research* (1997) 17(1A), 141-150.

Vincent, et al.; "Chemotherapy with DMXAA (5, 6-dimethylxanthenone-4-acetic acid) in combination with CI-1010 (1H-imidazole-1-ethanol, α-[[(2-bromoethyl)amino]methyl]-2-nitro-, mono-hydrobromide (R isomer)) against advanced stage murine colon carcinoma 26"; *Oncology Reports*; (1997) 4(1), 143-147.

Watts, et al.; "Changes in coagulation and permeability properties of human endothelial cells in vitro induced by TNF-α or 5, 6 MeXAA"; *British Journal of Cancer, Suppl.*; (1996) 74(27): S164-S167.

Wilson, et al.; "Tertiary amine N-oxides as bioreductive drugs: DACA N-oxide, nitracrine N-oxide and AQ4N"; *British Journal of Cancer Supplemental*; (1996) 74(27), S43-S47.

Pedley, et al.; "Ablation of Colorectal Xenografts with Combined Radioimmunotherapy and Tumor Blood Flow-modifying Agents"; *Cancer Research*; (1996) 56(14), 3293-3300.

William R. Wilson and Frederik B. Pruijn; "Hypoxia-Activated Prodrugs as Antitumour Agents: Strategies for Maximizing Tumor Cell Killing"; *Clinical and Experimental Pharmacology and Physiology*; (1995) 22(11), 881-885.

Hill, et al.; "Anti-Vascular Approaches to Solid Tumor Therapy: Evaluation of Vinblastine and Flavone Acetic Acid"; *Int. J. Cancer*; (1995) 63(1), 119-123.

Philpott, et al.; "Induction of tumor necrosis factor-α by single and repeated doses of the antitumour agent 5, 6-dimethylxanthenone-4-acetic acid"; *Cancer Chemother. Pharmacol.*; (1995) 36(2) 143-148.
Laws, et al.; "Preclinical in vitro and in vivo activity of 5, 6-dimethylxanthenone-4-acetic acid"; *British Journal of Cancer*; (1995) 71(6), 1204-1209.
Webster, et al.; "Metabolism and Elimination of 5, 6-Dimethylxanthenone-4-Acetic Acid in the Isolated Perfused Rat Liver"; *Drug Disposition, A Publication of The Amer. Soc. for Pharm. and Exper. Therapeutics*; (1995) 23(3): 363-368.
Perera, et al.; "Activation of LPS-Inducible Genes by the Antitumor Agent 5, 6-Dimethylxanthenone-4-Acetic Acid in Primary Murine Macrophages"; *The Journal of Immunology*; (1994) 153(10), 4684-4693.
Zwi, et al.; "The Morphological Effects of the Anti-Tumor Agents Flavone Acetic Acid and 5, 6-Dimethyl Xanthenone Acetic Acid on the Colon 38 Mouse Tumor"; *Pathology*; (1994) 26(2), 161-169.
Kestell, et al.; "Disposition of the novel antitumour agent xanthenone-4-acetic acid in the mouse: identification of metabolites and routs of elimination"; *Xenobiotica*; (1994) 24(7): 635-647.
Pedley, et al.; "Enhancement of Radioimmunotherapy by Drugs Modifying Tumor Blood Flow in a Colonic Xenograft Model"; *Int. J. Cancer*; (1994) 57(6), 830-835.
Everett, et al.; "Decarboxylation of the antitumour drugs flavone-8-acetic acid and xanthenone-4-acetic acid by nitrogen dioxide"; *Anti-Cancer Drug Design*; (1994) 9(1), 68-72.
Ching, et al.; "Effect of Tumor Growth on the Macrophage Response to the Antitumour Agent 5, 6-Dimethylxanthenone-4-acetic Acid"; *Anticancer Research*; (1993) 13(6A), 2069-2076.
Ching, et al.; "Induction of Tumor Necrosis Factor-α Messenger RNA in Human and Murine Cells by the Flavone Acetic Acid Analogue 5, 6-Dimethylxanthenone-4-acetic"; *Cancer Research*; (1994) 54(4), 870-872.
Thomsen, et al.; "Nitric Oxide: its production in host-cell-infiltrated EMT6 spheroids and its role in tumor cell killing by flavone-8-acetic acid and 5, 6-dimethylxanthenone-4-acetic acid"; *Cancer Chemother. Pharmacol.*, (1992) 31(2), 151-155.
Veszelovszky, et al.; "Flavone Acetic Acid and 5, 6-Dimethylxanthenone-4-acetic Acid: Relationship between Plasma Nitrate Elevation and the Induction of Tumor Necrosis"; *Eur. J. Cancer, Part A*; (1993) 29A(3): 404-408.
Gamage, et al.; "Structure-activity relationship for substituted 9-oxo-9, 10-dihydroacridine-4-acetic acids: analogues of the colon tumor active agent xanthenone-4-acetic acid"; *Anti-Cancer Drug Design*; (1992) 7(5), 403-414.
Ching, et al.; "Antitumour responses to flavone-8-acetic acid and 5, 6-dimethylxanthenone-4-acetic acid in immune deficient mice"; *Br. J. Cancer*; (1992); 66(1), 128-130.
Ching, et al.; "Stimulation of macrophage tumouricidal activity by 5, 6-dimethylxanthenone-4-acetic acid, a potent analogue of the antitumour agent flavone-8-acetic acid"; *Biochemical Pharmacology*; (1992) 44(1): 192-195.
Thomsen, et al.; "Modulation of superoxide production from murine macrophages by the antitumour agent flavone acetic acid and xanthenone acetic acid analogues"; *Biochemical Pharmacology*; (1992); 43(2): 386-389.
Ching, et al.; "In vitro Methods for Screening Agents with an Indirect Mechanism of Antitumour Activity: Xanthenone Analogues of Flavone Acetic Acid"; *Eur. J. Cancer*; (1991); 27(12) 1684-1689.
Ching, et al.; "Haematological effects in mice of the antitumour agents xanthenone-4-acetic acid, 5, 6-dimethylxanthenone-4-acetic acid and flavoneacetic acid"; *Cancer Chemother. Pharmacol.*; (1991) 28(6), 414-419.
Rewcastle, et al.; "Potential Antitumor Agents. 63. Structure-Activity Relationships for Side-Chain Analogues of the Colon 38 Active Agent 9-oxo-9H-xanthene-4-acetic Acid"; *J. Med. Chem.*; (1991) 34(9), 2864-2870.
Zwi, et al.; "Necrosis in non-tumor tissues caused by flavone acetic acid and 5, 6-dimethyl xanthenone acetic acid"; *Br. J. Cancer*; (1990) 62(6), 932-934.
Ching, et al.; "Induction of Natural Killer Activity by Xanthenone Analogues of Flavone Acetic Acid: Relation with Antitumour Activity"; *Eur. J. Cancer*; (1991); 27(1) 79-83.

Kestell, et al.; "Determination of xanthenone-4-acetic acid in mouse plasma by high-performance liquid chromatography"; *J. of Chromatography*; (1991) 564(1), 315-321.
Thomsen, et al.; "Evidence for the Production of Nitric Oxide by Activated Macrophages Treated with the Antitumor Agents Flavone-8-acetic Acid and Xanthenone-4-acetic Acid"; *Cancer Research*; (1990); 50(21), 6966-6970.
Rewcastle, et al.; "Potential Antitumor Agents. 61. Structure-Activity Relationships for in Vivo Colon 38 Activity among Disubstituted 9-oxo-9H-xanthene-4-acetic Acids"; *J. Med. Chem.*; (1991); 34(1), 217-222.
Rewcastle, Gordon W.; "Synthesis and Develpment of Two New Classes of Anticancer Drugs: the tricyclic Carboxamides and the xanthenoneacetic acids"; *Chemistry in New Zealand*; (1989); 53(6): 145-150.
Atwell, et al.; "Synthesis and anti-tumor activity of topologically-related analogues of flavoneacetic acid"; *Anti-Cancer Drug Design*; (1989); 4(2) 161-169.
Van der Auwera, et al.; "Conformational Features of Four Model Tripeptides having Piv-Pro-MeXaa-Nme$_2$ Sequences"; *Bull. Soc. Chim. Belg.*; (1988) 97(3): 199-207.
PCT International Sear Report for Application No. PCT/NZ00/00098 dated Oct. 31, 2000.
Cao Z. et al. "Thalidomide increases both intra-tumoural tumour necrosis factor-α production and anti-tumour activity in response to 5,6-dimethylxanthenone-4-acetic acid" *British Journal of Cancer* (1999) vol. 80(5/6), pp. 716-723.
Lissoni P. et al. "Neuroimmunotherapy of advanced solid neoplasms with simgle evening subcutaneous injection of low-dose interleukin-2 and melatonin Preliminary results" *European Journal of Cancer* (1993) vol. 29A(2), pp. 185-189.
European Search Report (European Appl. No. EP00942571) dated Mar. 18, 2003.
Databse WPI, Section CH, Week 199716, Derwent Publications Ltd., London, GB, XP002233615 & JP 09 040690, Feb. 10, 1997.
McLachlan et al., *The Potential of Cyclosporin A as an Anti-Tumor Agent*, Int. J. Immun., 1990, V. 12 (5), p. 469-479, XP009005663.
International Search Report PCT/NZ01/00154 dated Oct. 30, 2001.
Ching et al, Interaction between enxotoxin anf the antitumour agent 5, 6-dimethylxanthenone-4-acetic acid in the induction of tumour necrosis factor and haemorrhagic necrosis of colon 38 tumours, *Cancer Chemother. Pharmacol.*, 35:153-160 (1994).
Baguley, et al., "Small-Molecule Cytokine Inducers Causing Tumor Necrosis", Current Opinion in Investigational Drugs (2001), V. 2, No. 7, pp. 967-975.
Philpot, et al., "The Antitumour Agent 5, 6-Dimethylxanthenone-4-Acetic Acid Acts in vitro on Human Mononuclear Cells as a Co-Stimulator with Other Inducers of Tumour Necrosis Factor", European Journal of Cancer (2001), V. 37, No. 15, pp. 1930-1937.
Supplementary Partial European Search Report (EP01961455).
European Examination Report.
Supplementary Partial European Search Report (EP01961455), Dated May 9, 2005.
European Examination Report, Dated Aug. 25, 2005.
Supplementary Partial European Search Report (EP01961455), Dated Apr. 25, 2005.
U.S. Appl. No. 12/064,632, filed Aug. 28, 2006, Green et al.
U.S. Appl. No. 12/064,633, filed Aug. 25, 2006, Green et al.
Atwell, et al.; "Potential Antitumor Agents. 60. Relationships between Structure and in Vivo Colon 38 Activity for 5-Substituted 9-Oxoxanthene-4-acetic Acids"; 1990; J. Med. Chem.; 33: 1375-1379.
Avastin. Http://www.centerwatch.com/patient/drugs/dru851.html, Jun. 29, 2004.
Baguley, et al.; "Potential of DMXAA combination therapy for solid tumors"; 2005; Expert Rev. Anticancer Ther.; 2(5): 593-603.
Barefoot, R.; "Speciation of platinum compounds: a review of recent applications in studies of platinum anticancer drugs"; Journal of Chromatography B, 2001, 751:205-211.
Begley, et al.; "The Blood-Brain-Barrier: Principles for Targeting Peptides and Drugs to the Central Nervous System"; J. Pharm. Pharmacol 1996, 48:136-146.

Bibby, et al.; "Flavone acetic acid - from laboratory to clinic and back"; 1993; Anti-Cancer Drugs; 4: 3-17.

Bibby, et al., "Reduction of Tumor Blood Flow by Flavone Acetic Acid: A Possible Component of Therapy"; 1989; J. Natl. CAncer Inst.; 81:216-220.

Brem, et al.; "Interstitial chemotherapy with drug polymer implants for the treatment of recurring gliomas"; J. Neurosurg. 1991, 74:441-446.

Calabresi, et al.; "The Pharmacological Basis of Therapeutics, Ninth Edition," (1996), Goodman & Gilman's The Pharmacological Basis of Therapeutics. Section X, Chemotherapy of Neoplastic Diseases, pp. 1225-1229.

Ching, et al.; "The Anti-Tumour and Immune-Modulatory Activities of Flavone Acetic and Xanthone Acetic Acids"; 1990; N.P. Das (ed.), flavanoids in Biology and Medicine III. Proceedings of the 3rd International Symposium on Flavonoids in Biology and Medicine; 381-391.

Coloma, et al.; "Transport across the primate Blood-Brain-Barrier of a genetically engineered Chimeric Monoclonal Antibody to the Human Insulin Receptor"; Pharmaceutical Research 2000, 17(3):266-274.

Corbett, et al.; "Activity of flavone acetic acid (NSC-347512) against solid tumors of mice"; 1986; Investigational New Drugs; 4: 207-220.

Djeha, et al.; "Synergistic in vivo antitumor activity in lung and colon cancer xenografts with the vascular disrupting agent DMXAA combined with bevacizumab"; Proc. Am. Assoc. Cancer. Res. Annual Meeting, 2006, 47:55.

Graham, et al.; Fresh from the Pipeline: Cetuximab; Nature Reviews Drug Discovery 2004, 3:549-550.

Griffioen, et al.; "Angiogenesis Inhibitors Overcome Tumor Induced Endothelial Cell Anergy"; 1999; Int. J. Cancer; 80: 315-319.

Jameson, et al.; "Phase I Pharmacokinetic and Pharmacodynamic Study of 5,6-Dimethylxanthenone-4-Acetic Acid (DMXAA), A Novel Antivascular Agent"; 2000; Proc. Am. Soc. Clin Oncol.; 19: 182a.

Johnson, et al.; "Relationships between drug activity in NCI preclinical in vitro and in vivo models and early clinical trials." British J. of Cancer, 2001, 84(10):1424-1431.

Kelland, L.; "Targeting Established Tumor Vasculature: A Novel Approach to Cancer Treatment"; Curr.Cancer. Ther. Rev. 2005, 1(1):1-9.

Kroll, et al.; "Improving Drug Delivery to Intracerebral Tumor and Surrounding Brain in a Rodent Model: A Comparison of Osmotic versus Bradykinin Modification of the Blood-Brain and/or Blood-Tumor Barriers"; Neurosurgery 1998, 43(4):879-886.

Langer, R.; "New Methods of Drug Delivery". Science 1990, 249:1527-1533.

Marnett, L.J.; "Aspirin and Related Nonsteroidal Anti-inflammatory Drugs as Chemopreventive Agents against Colon Cancer," Preventive Medicine 24,103-106 (1995).

Marona, H.; "Synthesis and Properties of Some Xanthone-2-Alkylcarboxylic acids and Xanthone-2-Glyoxal." Polish Journal of Chemistry, 54:2059 (1980).

Nakanishiki, et al.; "Carboxylic Acids". Chem. Abstr. 76:126784w (1972), (Abstract of Japan A-7,200,425).

Nakanishi, et al.; "Studies of Anti-Inflammatory Agents XXXI; Studies on the Synthesis and Anti-Inflammatory Activity of Xanthenyl- and Benzo-pyranopyridinylacetic acid Derivatives." Yakugaku Zasshi, 96:99-109 (1976).

Neuwelt, et al.,; "Increased Delivery of Tumor-specific Monoclonal Antibodies to Brain after Osmotic Blood-Brain-Barrier modification in Patients with Melanoma Metastatic to the Central Nervous System"; Neurosurgery 1987, 20(6):885-895.

Nishino, et al.; "Oxidation of 9-Xanthenones with Lead (IV) Acetate. Formation of Di-gamma-lactones." Bull. Chem Soc. Jpn. 56:2847-48 (1983).

Nishino, et al.; "Regioselective Carboxylation of 9-Xanthenones with Manganese (III) Acelate." Bull. Chem Soc. Jpn. 56:474-480 (1983).

O'Reilly, et al.; "Endostatin: An Endogenous Inhibitor of Angiogenesis and Tumor Growth"; 1997; Cell; 88: 277-285.

Peckham, et al.; "Oxford Textbook of Oncology". Oxford University Press, vol. 1. p. 451, 1995.

Plowman, et al.; "Flavone Acetic Acid: A Novel Agent with Preclinical Antitumor Activity Against Colon Adenocarcinoma 38 in Mice"; 1986; Cancer Treatment Reports; 70(5): 631-635.

PTCL. Chemical and Other Safety Information. "ptcl.chem.ox.ac.uk/MSDS" 2007.

Rewcastle, et al.; "Potential Antitumor Agents. 62. Structure-Activity Relationships for Tricyclic Compounds Related to the Colon Tumor Active Drug 9-Oxo-9H-xanthene-4-acetic Acid"; 1991; J. Med. Chem.; 34: 491-496.

Rustin et al.; "5,6-Dimethylxanthenone-4-acetic (DMXAA), a novel antivascular agent: phase I clinical and pharmacokinetic study." British Journal of Cancer, 2003, vol. 88, pp. 1160-1167.

Rustin et al.; "Impact on Tumour Perfusion Measured by Dymanic Magnetic Resonance Imaging (MRI), in the Phase 1 Trial of 5,6-dimethylxanthenone-4-acetic Acid (DMXAA)"; Proc. 10th NCI-EORTC Symp. New Drugs; 1998; 10:126.

Saltiel, E.; "Erlotinib". Http://www.medicinenet.com/erlotinib/article.htm. Nov. 28, 2004.

Saltiel, E.; "Erlotinib". Http://www.medicinenet.com/erlotinib/article.htm. Jun. 22, 2005.

Sausville, et al.; "Contributions of human tumor xenografts to anti-cancer drug development." Cancer Research, 2006, vol. 66(7), pp. 3351-3354.

Shoemaker, et al.; "Pleiotropic Rsistance and Drug Development"; 1986; Cancer Drug Resistance; 143-149.

Showalter, H.; "Potential Antitumor Agents. 61. Structure-Activity Relationships for In Vivo Colon 38 Activity Among Disubstituted 9-Oxo-9H-xanthene-4-acetic acids"; 1991; Chemtracts: Org. Chem. 4(2): 168-171. Commentary of Rewcastle: J. Med. Chem. 1991, 34:217.

Siemann, et al.; "Enhanced Antitumor Efficacy through the combination of Vascular Targeting Agents and Conventional Anticancer Drugs". Proceedings of the American Association for Cancer Research, 2000, vol. 41, p. 525.

Siemann, et al.; "Vascular Targeting Agents Enhance Chemotherapeutic Agent Activities in Solid Tumor Therapy", Int. J. Cancer: 99, 1-6 (2002).

Siim, et al.; Marked potentiation of the antitumor activity of chemotherapeutic drugs by the antivascular agent 5,6-dimethylxanthenone-4-acetic acid (DMXAA); 2003; Cancer Chemother Pharmacol; 51: 43-52.

Simone, et al.; "Oncology". Cecil Text Book of Medicine. 20th Edition vol. 1, W. B. Saunders Company. 1997, p. 1004-1010.

Temsamani, et al.; "Brain drug delivery technologies: novel approaches for transporting therapeutics"; Pharm. Sci. Technology Today 2000, 3(5):155-162.

Tyle, P.; "Iontophoretic Devices for Drug Delivery"; Pharmaceutical Research 1986, 3(6):318-326.

Van Moorsel, et al.; "Combination Chemotherapy Studies with Gemcitabine and Etoposide in Non-Small Cell Lung and Ovarian Cancer Cell Lines." Biochemical Pharmacology, 1999, vol. 57, pp. 407-415.

Westland, et al.; "Activated non-neural specific T cells open the blood-brain-barrier to circulating antibodies"; Brain 1999, 122:1283-1291.

Wilkinson, et al.; "Tamoxifen (Noivadex*) Therapy - Radionale for Loading Dose Followed by Maintenance Dose for Patients with Metastatic Breast Cancer." Cancer Chemotherapy Pharmacol. (1982) 10, 33-35.

Wouters, et al.; "Hypoxia as a target for combined modality treatments"; 2002; European J. of Cancer; 38: 240-257.

Zaharko, et al.; Therapeutic and Pharmacokinetic Relationships of Flavone Acetic Acid: An Agent with Activity Against Solid Tumors; 1986; Cancer Treatment Reports; 70(12): 1415-1421.

Zhang, et al.; "Conjugation of brain-derived neurotrophic factor to a blood-brain-barrier resistant drug targeting system enables neuroprotection in reginal brain ischemia following intravenous injection of the neurotrophin."; Brain Research 2001, 889:49-56.

Zhao, et al.; "Improvement of the antitumor activity of intraperitoneally and orally administered 5,6-dimethylxanthenone-4-acetic acid by optimal scheduling." Clinical Cancer Research, 2003, vol. 9, pp. 6545-6550.

Zhao, et al.; "Oral activity and pharmacokinetics of 5,6-dimethylxanthenone acetic acid (DMXAA) in mice"; Cancer Chemother. Pharmacol. (2002), 49, 20-26.

Zhou, et al.; "5,6-dimethylxanthenone-4-acetic acid (DMXAA): a new biological response modifier for cancer therapy"; Invest New Drugs. Aug. 2002;20(3):281-95.

Zhou, et al.; "Effects of anticancer drugs on the metabolism of the anticancer drug 5,6-dimethylxanthenone-4-acetic (DMXAA) by human liver microsomes"; 2001; J. Clin. Pharmacol.; 52: 129-136.

Zwi, et al.; "Blood Flow Failure as a Major Determinant in the Antitumor Action of Flavone Acetic Acid"; 1989; J. Natl. Cancer Inst.; 81: 1005-1013.

* cited by examiner

CANCER TREATMENT BY COMBINATION THERAPY

RELATED APPLICATIONS

This application is a continuation of International Application PCT/NZ01/00154, filed Jul. 27, 2001, which claims priority from New Zealand Application No. 506060, filed Jul. 28, 2000.

FIELD OF THE INVENTION

This invention relates to a method of treating cancer and to compositions of use in such a method.

BACKGROUND OF THE INVENTION

The xanthenone acetic acid class of compounds have been shown to be of potential utility in cancer treatment. Of these, the compound 5,6-dimethylxanthenone-4-acetic acid (DMXAA) has been shown to have significant antitumour activity against murine tumours. Studies in animals have shown that this activity is a consequence of the induction of the cytokine tumour necrosis factor (TNF), particularly within tumour tissue, and of the consequent inhibition of tumour blood flow. To date, DMXAA has shown evidence of marginal clinical anti-cancer activity in humans.

The applicants have now surprisingly found that DMXAA amplifies the induction of TNF by cultured human peripheral blood cells in response to a variety of agents capable of inducing a second signal that by itself modulates TNF production. These include ligands that occupy external cellular receptors connected with the TNF induction pathway and compounds that modulate cellular biochemical pathways connected to TNF induction.

With the above background in mind, it is an object of the present invention to provide a method of treatment of cancer which will at least provide the public with a useful choice.

SUMMARY OF THE INVENTION

Accordingly, in a first aspect, the present invention provides a method of treating cancer, the method including the step of administering to a mammal in need of such treatment, either simultaneously or sequentially:

(i) a compound of the formula (I)

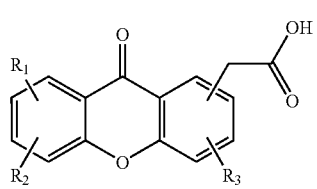

(I)

or a pharmaceutically acceptable salt or ester thereof, wherein $R_1$, $R_2$ and $R_3$ are each independently selected from the group consisting of H, $C_1$-$C_6$ alkyl, halogen, $CF_3$, CN, $NO_2$, $NH_2$, OH, OR, NHCOR, $NHSO_2R$, SR $SO_2R$ or NHR, wherein each R is independently $C_1$-$C_6$ alkyl optionally substituted with one or more substituents selected from hydroxy, amino and methoxy, and wherein each of $R_1$, $R_2$ and $R_3$ may be present at any of the available positions 1 to 8;

and wherein in each of the carbocyclic aromatic rings in formula (I), up to two of the methine (—CH=) groups may be replaced by an aza (—N=) group;

and wherein any two of $R_1$, $R_2$ and $R_3$ may additionally together represent the group —CH=CH—CH=CH—, such that this group, together with the carbon or nitrogen atoms to which it is attached, forms a fused 6 membered aromatic ring, and (ii) a compound selected from compounds which modulate TNF production and compounds which act on biochemical pathways leading to TNF synthesis.

Preferably, the mammal is a human.

In certain preferred embodiments, the compound (ii) is a ligand that binds to the CD14 receptor of cells, such as bacterial LPS, deacylated LPS and CD14 receptor antibodies.

In other preferred embodiments, the compound (ii) is a ligand that binds to a surface receptor of cells connected with TNF production other than the CD14 receptor, such as interleukin-1 alpha.

In other preferred embodiments, the compound (ii) is a compound that induces protein kinase C, such as phorbol myristate ester.

In other preferred embodiments, the compound (ii) is a compound that can decrease the activity of protein phosphatases, preferably protein phosphatase 2A, such as okadaic acid.

Preferably, compound (i) is of the formula (Ia):

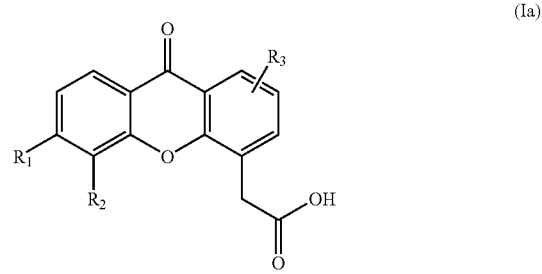

(Ia)

wherein $R_1$, $R_2$ and $R_3$ are as defined for the compound of formula (I) above.

Most preferably, the compound of formula (I) or (Ia) is 5,6-dimethylxanthenone-4-acetic acid, having the formula

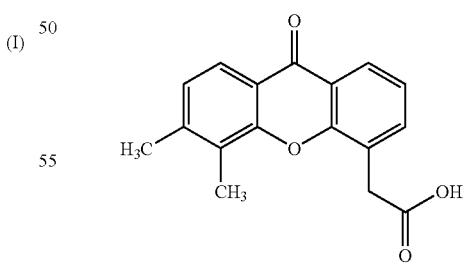

DMXAA

In a further aspect, the present invention provides the use of a compound (i) of the formula (I) as defined above, or a pharmaceutically acceptable salt or ester thereof, in the manufacture of a medicament for treating cancer in a mammal by sequential or simultaneous co-administration of the medicament and a compound (ii) selected from compounds which modulate TNF production and compounds which act on biochemical pathways leading to TNF synthesis.

Preferably the compound (i) is DMXAA.

Preferably compound (ii) is selected from a ligand that binds to the CD14 receptor of cells; a ligand that binds to a surface receptor of cells connected with TNF production other than the CD14 receptor; a compound that induces protein kinase C; or a compound that can decrease the activity of protein phosphatases.

In still a further aspect, the present invention provides the use of a compound (ii) selected from compounds which modulate TNF production and compounds which act on biochemical pathways leading to TNF synthesis, in the manufacture of a medicament for treating cancer in a mammal by sequential or simultaneous co-administration of the medicament and a compound (i) of the formula (I) as defined above, or a pharmaceutically acceptable salt or ester thereof.

Preferably the compound (i) is DMXAA.

Preferably compound (ii) is selected from a ligand that binds to the CD14 receptor of cells; a ligand that binds to a surface receptor of cells connected with TNF production other than the CD14 receptor; a compound that induces protein kinase C; or a compound that can decrease the activity of protein phosphatases.

In yet a further aspect, the present invention provides a pharmaceutical composition suitable for treating cancer, the composition including a compound (i) of the formula (I) as defined above or a pharmaceutically acceptable salt or ester thereof; and a compound (ii) selected from compounds which modulate TNF production and compounds which act on biochemical pathways leading to TNF synthesis, in combination with one or more pharmaceutically acceptable carriers or vehicles.

Preferably the compound (i) is DMXAA.

Preferably compound (ii) is selected from a ligand that binds to the CD14 receptor of cells; a ligand that binds to a surface receptor of cells connected with TNF production other than the CD14 receptor; a compound that induces protein kinase C; or a compound that can decrease the activity of protein phosphatases.

Preferably the composition is formulated for co-administration of compounds (i) and (ii), or is formulated for sequential administration of compounds (i) and (ii) in any order.

DESCRIPTION OF THE DRAWINGS

While the invention is broadly as defined above, it also includes embodiments of which the following description provides examples. These specific embodiments are described in conjunction with the accompanying drawings in which.

DESCRIPTION OF THE INVENTION

Figure 1:
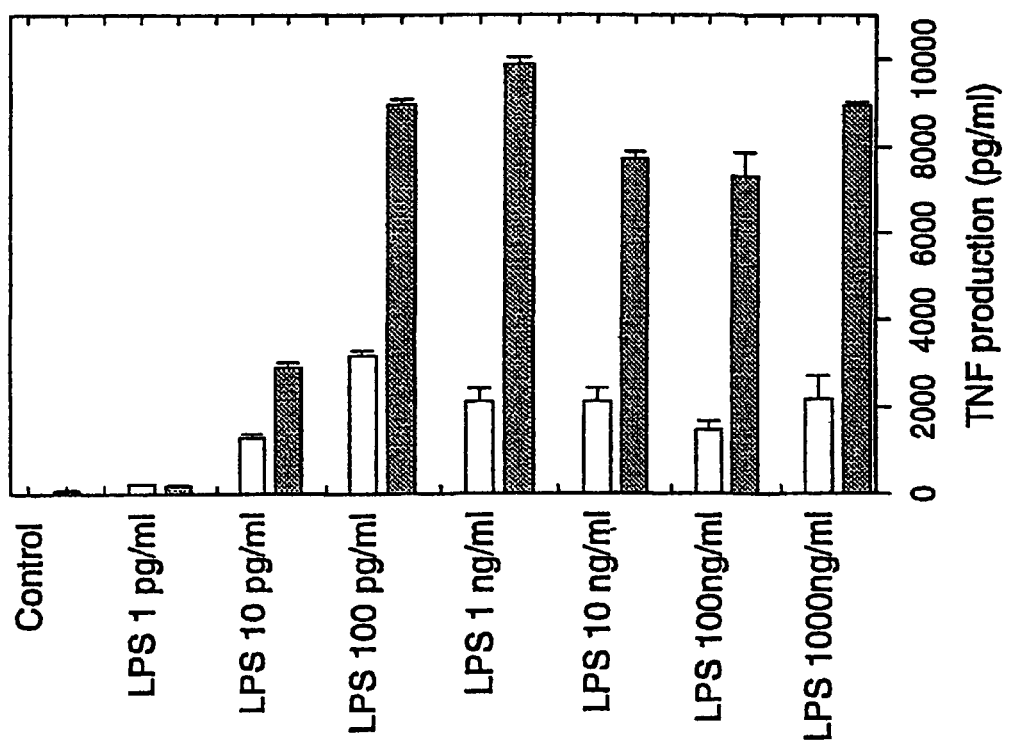
FIG. 1 shows the effect of DMXAA on LPS-induced TNF production in HPBL in vitro. HPBL were incubated (8 h) with the indicated concentrations of LPS alone (no shading) or in combination with DMXAA (shading). Supernatants were then removed and assayed for TNF content.
Figure 2:
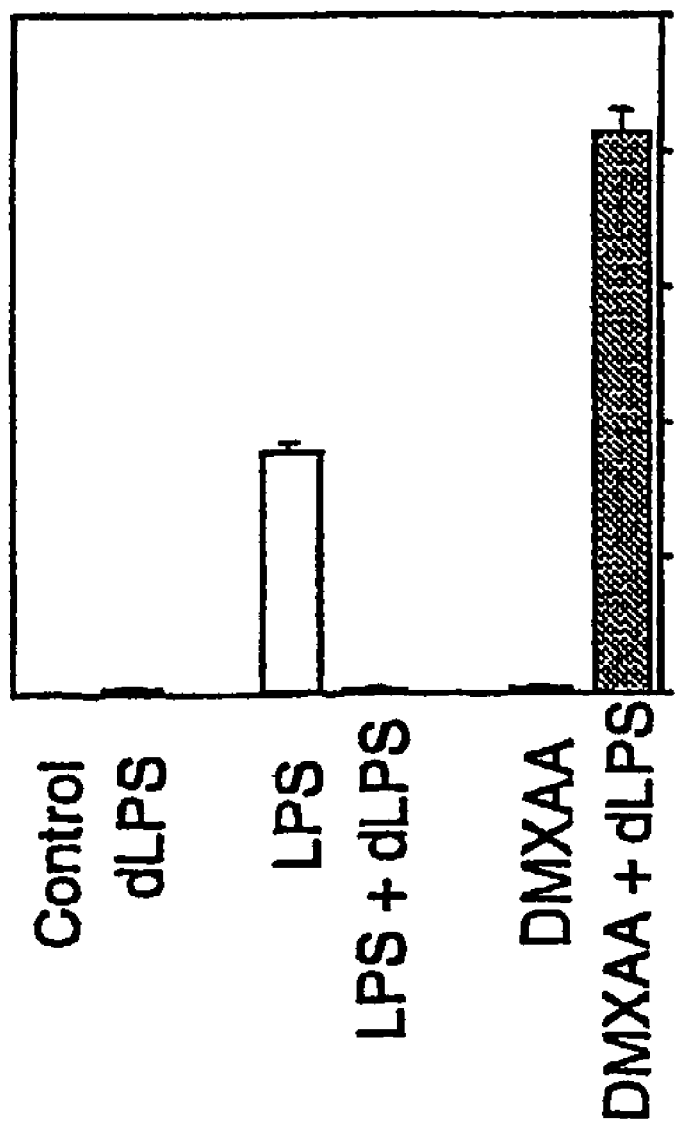
FIG. 2 shows the effect of DMXAA on dLPS-induced TNF production in HPBL in vitro. HPBL were incubated (8 h) with the indicated concentrations of dLPS alone (light bars) or in combination with DMXAA (shaded bars). Supernatants were then removed and assayed for TNF content. Horizontal lines represent the SEM.
Figure 3:
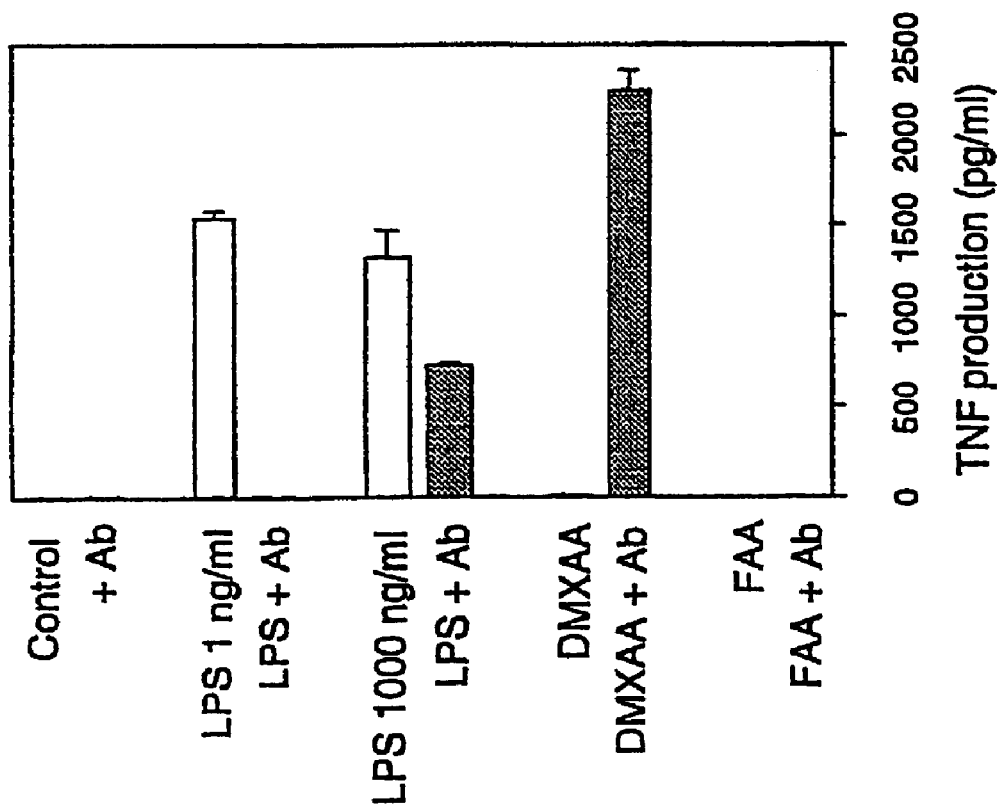
FIG. 3 shows the effect of anti-CD 14 antibodies on DMXAA- and LPS-induced TNF production in HPBL in vitro. HPBL were incubated (8 h) with LPS (1 ng/ml or 1 μg/ml), DMXAA (800 μg/ml) or flavone acetic acid (FAA) (800 μg/ml) in the absence (no shading) or the presence (shading) of anti-CD14 antibodies. Supernatants were then removed and assayed for TNIF content. Horizontal lines represent the SEM.

As defined above, the present invention relates to a method of treating cancer and to compositions of use in such a method.

The invention resides in the applicant's unexpected finding of a very large synergistic interaction in cultured human peripheral blood cells between compounds of the xanthenone acetic acid class having the formula (I) as defined below and compounds capable of contributing to the control pathway that modulates TNF (tumour necrosis factor) synthesis in human cells, that is, compounds that themselves modulate TNF production or compounds which are capable of acting on pathways leading to TNF synthesis.

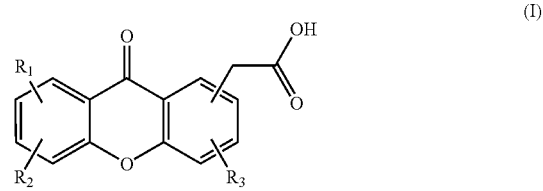

or a pharmaceutically acceptable salt or ester thereof, wherein $R_1$, $R_2$ and $R_3$ are each independently selected from the group consisting of H, $C_1$-$C_6$ alkyl, halogen, $CF_3$, CN, $NO_2$, $NH_2$, OH, OR, NHCOR, $NHSO_2R$, SR, $SO_2R$ or NHR, wherein each R is independently $C_1$-$C_6$ alkyl optionally substituted with one or more substituents selected from hydroxy, amino and methoxy, and wherein each of $R_1$, $R_2$ and $R_3$ may be present at any of the available positions 1 to 8;

and wherein in each of the carbocyclic aromatic rings in formula (1), up to two of the methine (—CH=) groups may be replaced by an aza (—N=) group;

and wherein any two of $R_1$, $R_2$ and $R_3$ may additionally together represent the group —CH=CH—CH=CH—, such that this group, together with the carbon or nitrogen atoms to which it is attached, forms a fused 6 membered aromatic ring.

In particular, the simultaneous administration of a compound of formula (I) 5,6-dimethylxanthenone-4-acetic acid (DMXAA) and a compound capable of contributing to the control pathway that modulates TNF synthesis in human cells, shows greater induction of TNF in cultured human peripheral blood cells than either agent alone. TNF has recognised anticancer activity and can act either directly on cancer cells or indirectly on the cancer's blood supply.

It is shown herein that while DMXAA alone has little effect on TNF induction in cultured human peripheral blood leucocytes (HPBL), its combination with compounds that contribute to TNF induction surprisingly achieves effects dramatically larger than for either agent alone, and greatly exceeds the sum of effects of the individual agents. The combination of DMXAA or other compounds of the formula (I) (as described above) with a second agent acting on the TNF pathway is therefore expected to have clinical utility in cancer treatment. Further studies are needed to confirm that all compounds of formula (I) will act in a similar manner to DMXAA, but at this stage there is little reason to presume that DMXAA will be alone amongst the xanthenone acetic acid compounds in its effect in combination with the compounds (ii).

The compounds of the formula (I) are known and can be prepared using methods known to those persons skilled in the art. For example, compounds of the formula (I) and their preparation are described in the following references:

Journal of Medicinal Chemistry 34(1): 217-22, January, 1991;
Journal of Medicinal Chemistry 34(2): 491-6, February, 1991;
Journal of Medicinal Chemistry 33(5): 1375-9, May, 1990;
Journal of Medicinal Chemistry 34(9): 2864-70, September, 1991; and
Journal of Medicinal Chemistry 32(4): 793-9, April, 1989, the contents of which are incorporated herein by reference.

Of the compounds of formula (I) defined above, compounds of the formula (Ia) as described below (in which the substituents $R_1$ and $R_2$ are at the 5- and 6-positions), are generally preferred for use in the methods of the invention.

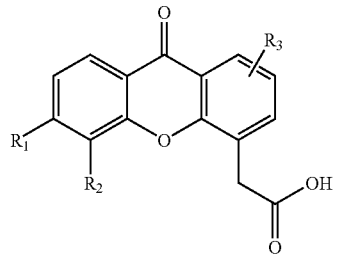

(Ia)

wherein $R_1$, $R_2$ and $R_3$ are as defined for the compound of (I) above.

A particularly preferred compound is 5,6-dimethylxanthenone-4-acetic acid (DMXAA). The preparation of this compound is described in Journal of Medicinal Chemistry 34(1): 217-22, January, 1991.

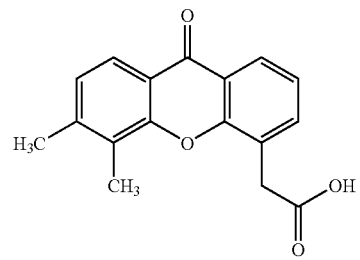

DMXAA

The compounds capable of contributing to the control pathway that modulates TNF synthesis in human cancer tissue described above are also well known compounds (see, for example, Philpott M, Ching L M, Baguley B C; Eur J Cancer 2001, in press) and can likewise be prepared by methods known to those skilled in the art. As will be readily apparent, more than one of those compounds can be combined with the compound(s) of formula (I) or (Ia). Reference to "a compound" should not be seen to be restrictive to only one such compound.

In certain embodiments of the invention, the compound capable of contributing to the control pathway that modulates TNF synthesis is a ligand that binds to the CD14 receptor of cells. Examples of such ligands are bacterial lipopolysaccharide (LPS), deacylated lipopolysaccharide (dLPS), and antibodies to the CD14 receptor for LPS and dLPS.

In further embodiments of the invention, the compound capable of contributing to the control pathway that modulates TNF synthesis is a compound that acts on surface receptors, other than CD14 receptors, that are connected with TNF production. An example of such a compound is interleukin-1 alpha (IL-1).

In still further embodiments of the invention, the compound is capable of contributing to the control pathways that modulate TNF synthesis by inducing the enzyme protein kinase C. Examples of such compounds are phorbol myristate esters such as phorbol myristate acetate.

In still further embodiments of the invention, the compound is capable of decreasing the activity of protein phosphatases, preferably protein phosphatase 2A. An example of such a compound is okadaic acid.

The therapeutic methods of the present invention therefore include the step of administering to a patient, simultaneously or sequentially, an agent capable of contributing to the control pathway that modulates TNF synthesis, and a compound of the formula (I) as defined above or a pharmaceutically acceptable salt or ester thereof.

The compound of formula (I) and the compound capable of contributing to the control pathway that modulates TNF synthesis can be administered to a patient in any suitable form. For example, the compounds may conveniently be administered intravenously, using formulations for each compound already known in the art. The formulation of medicaments for use in cancer treatment utilising combinations of the compounds referred to herein, together with pharmaceutically acceptable carriers, vehicles and excipients would be well within the abilities of a person skilled in this art. One known precaution would be to protect solutions of the highly water soluble DMXAA compound from light.

The compounds of formula (I) and the compound capable of contributing to the control pathway that modulates TNF synthesis can be administered either simultaneously or sequentially, i.e. the compound capable of contributing to the control pathway that modulates TNF synthesis can be administered either before or after the compound of formula (I) is administered. Simultaneous co-administration, in most cases, is likely to be preferred.

The invention will now be described in more detail with reference to the following non-limiting examples. While the examples have been directed to specific combinations of compounds it will be appreciated by those skilled in this art that the results are not restrictive to those compound combinations only.

EXAMPLES

Methods

Incubation of HPBL with drugs

Partially purified buffy coats were purchased from Auckland Blood Centre and divided into 15-ml aliquots in 50-ml centrifuge tubes (2070 Conical Tubes, Becton Dickinson Labware, N.J., USA). HPBL in tissue culture dishes (10 ml; $10^7$ cells/ml) were incubated overnight in α-MEM culture medium supplemented with FCS (10% v/v), streptomycin sulphate (100 μg/ml) and penicillin-G (100 units/ml). All extraction operations were carried out at 7° C. to prevent clotting. Unsupplemented α-MEM medium was added to 30 ml and a 10-ml layer of Ficoll-Paque PLUS was slowly added to the bottom of the tubes. After centrifugation at 300 g for 30 min the upper layer was removed and the HPBL layer was carefully drawn off into a fresh 50-ml centrifuge tube. The volume was adjusted to 50 ml, the cells were centrifuged at 300 g, and HPBL were resuspended in supplemented α-MEM medium and added (1 ml/well) to 24 well plates (Nunc, Kamstrup, Roskilde, Denmark). Agents (made up at twice the final concentration) were added and plates were incubated for the appropriate times in 5% $CO_2$/air at 37° C. overnight. DMXAA sodium salt (this laboratory) was dissolved in medium and protected from light FAA (National Cancer Institute, USA) was dissolved in 5% (w/v) sodium bicarbonate and diluted with medium. Interleukin-1aipha (R&D Systems, USA), okadaic acid, LPS and deacylated LPS (Sigma Chemical Co., USA) were dissolved in α-MEM, filter-sterilised and used immediately. The MEM-18 mouse anti-human CD14 IgG antibody was obtained from Sanbio bv, am Uden, Netherlands, and was freed from azide before use by ultrafiltration.

Measurement of TNF

After the appropriate incubation period of HPBL with drug, supernatants were either used immediately or stored at −20° C. TNF standards were prepared by making serial dilutions of the TNF stock solution in supplemented culture media (concentration range 10-10,000 pg/ml). ELISA plates were made using the OptEIA Human TNF-alpha Set (Pharmingen, San Diego, Calif., USA). TNF standards and samples were added to the ELISA plates and the assays were carried out according to the makers' directions.

Example 1

The induction of TNF in peripheral blood monocytes by low concentrations of the bacterial cell wall lipopolysaccharide (LPS) was unexpectedly stimulated by DMXAA. LPS has a large range of biological effects including antitumor effects (Raetz C R H, Ulevitch R J, Wright S D, Sibley C H, Ding A H, Nathan C F. *FASEB J* 1991, 5, 2652-2660). Certain bacteria can localise in tumour tissue (Kimura N T, Taniguchi S, Aoki K, Baba T, Cancer Res. 1980, 40, 2061-2068) and would therefore provide a localised LPS signal. Co-administration of DMXAA would amplify this signal.

Example 2

The induction of TNF by low local concentrations of the modified bacterial cell wall components, which by themselves do not stimulate TNF production, may be stimulated by DMXAA. Such components are included in genetically modified bacteria that might localise in tumour tissue but produce an attenuated systemic response, thus eliminating endotoxic shock as a side effect of such therapy (Low K B, Ittensohn M, Le T, Platt J, Sodi S. Amoss M, Ash O, Carmichael E, Chakraborty A, Fischer J, Lin S L, Luo X, Miller S I, Zheng L M, King I, Pawelek J M, Bermudes D, Nature Biotechnology, 1999, 17, 37-41.

The induction of TNF in peripheral blood monocytes by deacylated LPS (dLPS), an inactive form of LPS, was unexpectedly stimulated by DMXAA. dLPS does not alone induce TNF, and competitively inhibits the induction of TNF by LPS by competition for the CD14 receptor (Riedo F X, Munford R S, Campbell W B, Reisch J S, Chien K R, Gerard R D. *J Immunol* 1990, 144, 3506-3512). dLPS (500 μg/ml; 15 minutes pre-incubation) only slightly induced TNF production above the controls. dLPS also strongly reduced TNF production in response to LPS (1 ng/ml). DMXAA alone (800 μg/ml) caused no substantial induction of TNF. However the combination of dLPS (500 μg/ml; 15 minutes pre-incubation) and DMXAA (800 μg/ml) caused a large increase in TNF production.

Example 3

The induction of TNF in peripheral blood monocytes by an antibody (MEM-18) to the LPS receptor, CD14, was unexpectedly stimulated by DMXAA. Anti-CD14 antibody does not alone induce TNF alone and inhibits the induction of TNF by LPS (Devitt A, Moffatt O D, Raykundalia C, Capra J D, Simmons D L, Gregory C D, Nature 1998, 392, 505-509).

Example 4

Figure 4:
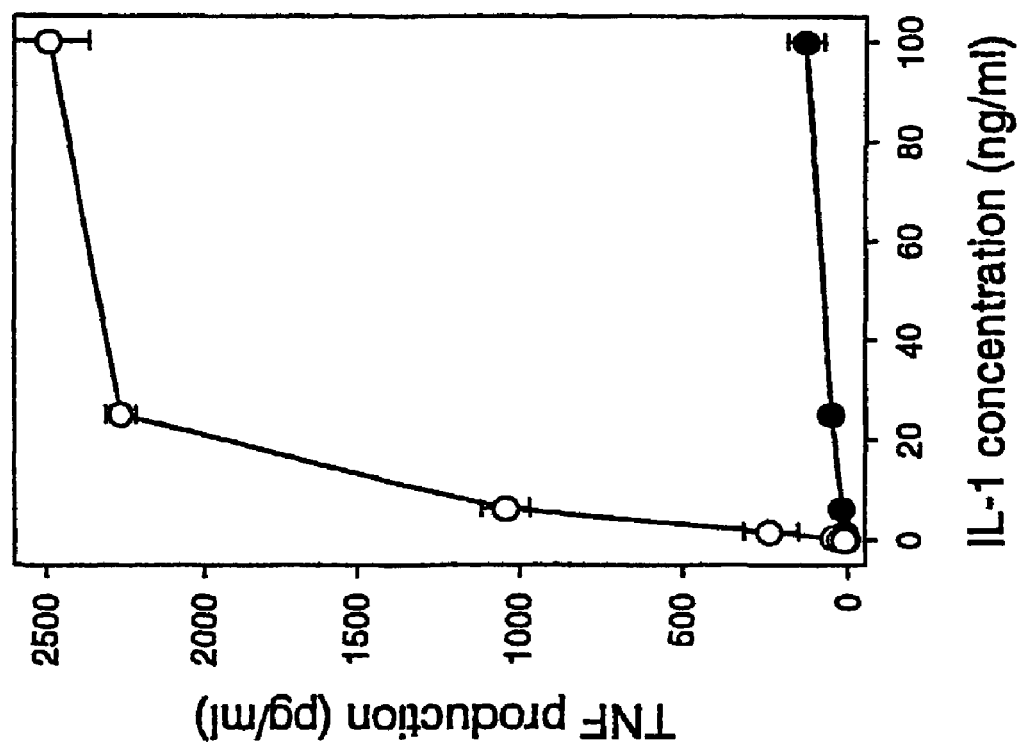
FIG. 4 shows the effect of DMXAA on TNF production in HPBL in vitro in response to interleukin-1alpha. HPBL were incubated (8 h) with the indicated concentrations of drug either alone (filled symbols) or in combination with DMXAA (unfilled symbols). Supernatants were then removed and assayed for TNF content. Vertical lines represent the SEM.
Figure 5:
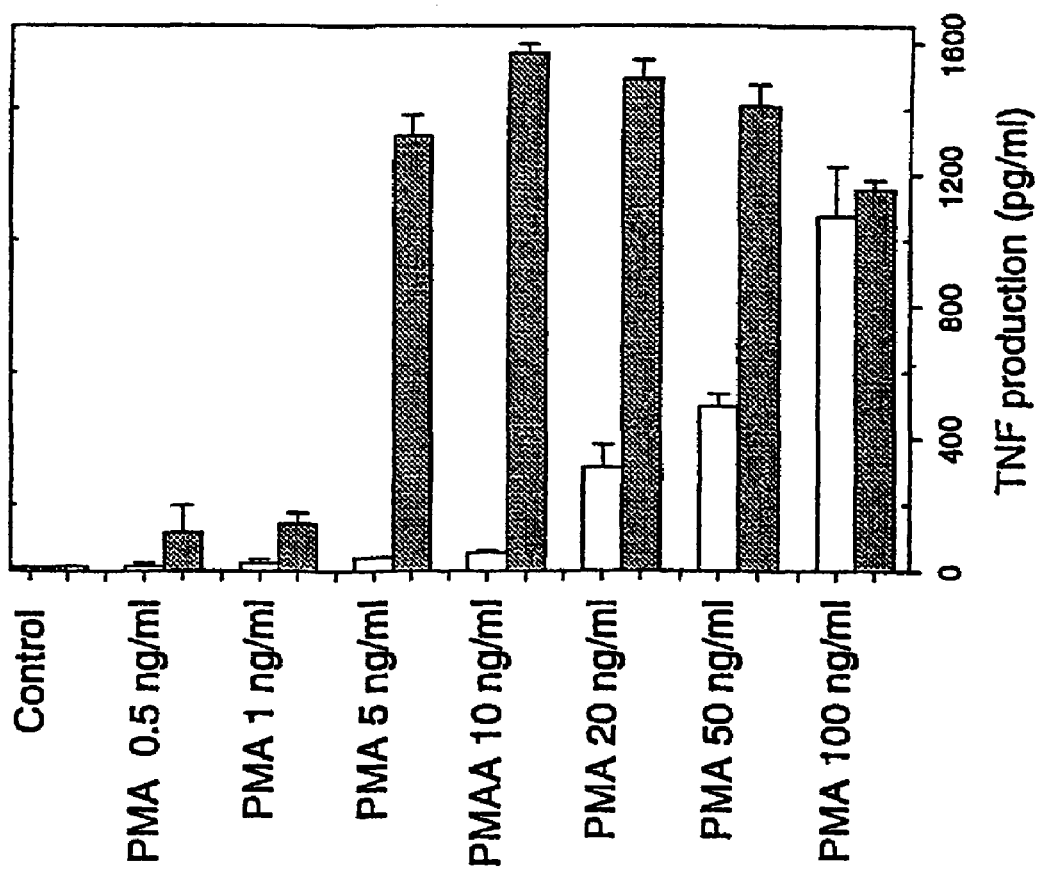
FIG. 5 shows the effect of DMXAA on TNF production in HPBL in vitro in response to phorbol-12-myristate-13-acetate. HPBL were incubated (8 h) with the indicated concentrations of drug either alone (unshaded) or in combination with DMXAA (shaded). Supernatants were then removed and assayed for TNF content. Horizontal lines represent the SEM.
Figure 6:
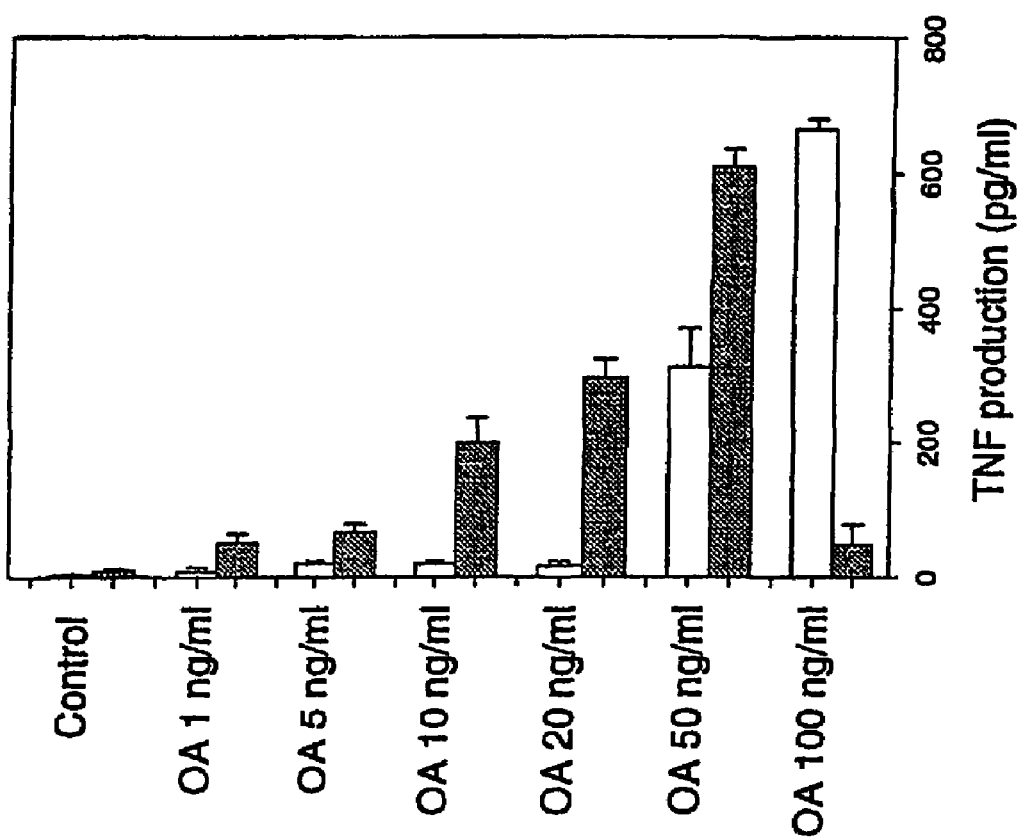
FIG. 6 shows the effect of DMXAA on TNF production in HPBL in vitro in response to okadaic acid. HPBL were incubated (8 h) with the indicated concentrations of drug either alone (unshaded) or in combination with DMXAA (shaded). Supernatants were then removed and assayed for TNF content. Horizontal lines represent the SEM.

The induction of TNF in peripheral blood monocytes by cytokines such as interleukin-1 (IL-1) was unexpectedly stimulated by DMXAA. The cytokine IL-1 is an inflammatory cytokine that itself has been reported to have experimental antitumor activity (Braunschweiger P G, Johnson C S, Kumar N, Ord V, Furmanski P, Cancer Res. 1988 48, 6011-6016). As shown in FIG. 4, IL-1 alone is capable of inducing TNF in human peripheral blood leukocytes (HPBL). However, coadministration of DMXAA greatly increases (up to 56-fold in this case) the induction of TNF as compared to that by IL-1 alone.

Example 5

The induction of TNF by low molecular weight activators of protein kinase C such as phorbol myristate acetate (PMA) was unexpectedly enhanced by co-administration of DMXAA. When HPBL were incubated with PMA alone at concentrations up to 20 ng/ml, there was no substantial induction of TNF. DMXAA alone (800 μg/ml) also had no substantial effect, DMXAA but in combination with PMA induced a higher degree of TNF production. At concentrations higher than 20 ng/ml, PMA alone induced TNF synthesis, as has been reported by others (Dong Z Y, Lu S, Zhang Y H. *Immunobiol* 1989, 179, 382-394).

Example 6

The induction of TNF by low molecular weight protein phosphatase inhibitors such as okadaic acid (OA), was unexpectedly enhanced by co-administration of DMXAA. When HPBL were incubated with OA alone at concentrations up to 20 ng/ml, there was no substantial induction of TNF. DMXAA alone (800 μg/ml) also had no substantial effect, DMXAA but in combination with OA induced a higher degree of TNF production. At concentrations higher than 20 ng/ml, OA alone induced TNF synthesis, as has been reported by others (Sung SSJ, Walters JA, Fu SM, J. Exp. Med. 1992, 176, 897-901).

Example 7

The effect of DMXAA on cultured murine leucocytes has also been investigated using LPS as a control. TNF was measured by enzyme-linked immunosorbent assay after 8 h.

Materials

DMXAA sodium salt (this laboratory) was dissolved in medium and protected from light (9). LPS and deacylated LPS (Sigma Chemical Co., MO) were dissolved in α-MEM, filter-sterilised and used immediately. The MEM-18 mouse anti-human CD14 IgG antibody was obtained from Sanbio by, am Uden, Netherlands, and was freed from azide before use by ultrafiltration and was LPS-free (Endospecy ES-50M LPS quantitation system, Seikagaku Corporation, Tokyo, Japan).

Extraction of Murine Leucocytes

Blood samples for extraction of leucocytes were taken by cardiac puncture of halothane-anaesthetised mice into 1-ml syringes containing ACD-A anticoagulant (0.1 ml). All extraction operations were carried out at 7° C. to prevent clotting. Samples were pooled and unsupplemented α-MEM was added to 30 ml and a 10-ml layer of Ficoll-Paque PLUS™ was slowly added to the bottom of the tubes. After centrifugation at 300×g for 30 min the upper layer was removed and the leucocyte layer was carefully drawn off into a fresh 50-ml centrifuge tube. The volume was adjusted to 50 ml with unsupplemented growth medium, the cells were centrifuged at 300×g, and the leucocytes were resuspended at $10^7$ cells/ml in α-MEM supplemented with foetal bovine serum (10% v/v), streptomycin sulphate (100 μg/ml) and penicillin-G (100 units/ml).

In Vitro Studies with Murine Leucocytes

Cells were added either to 24 well plates (1 ml/well; Nunc, Kamstrup, Roskilde, Denmark) or to 100 mm Petri dishes (10 ml/plate) and incubated in 5% $CO_2$/air at 37° C. overnight. Agents (made up at twice the final concentration in growth medium) were added and plates were further incubated for 8 hours. After the appropriate incubation period of HPBL with drug in 24-well plates, supernatants were removed and either assayed immediately or stored at −20° C.

Figure 7:
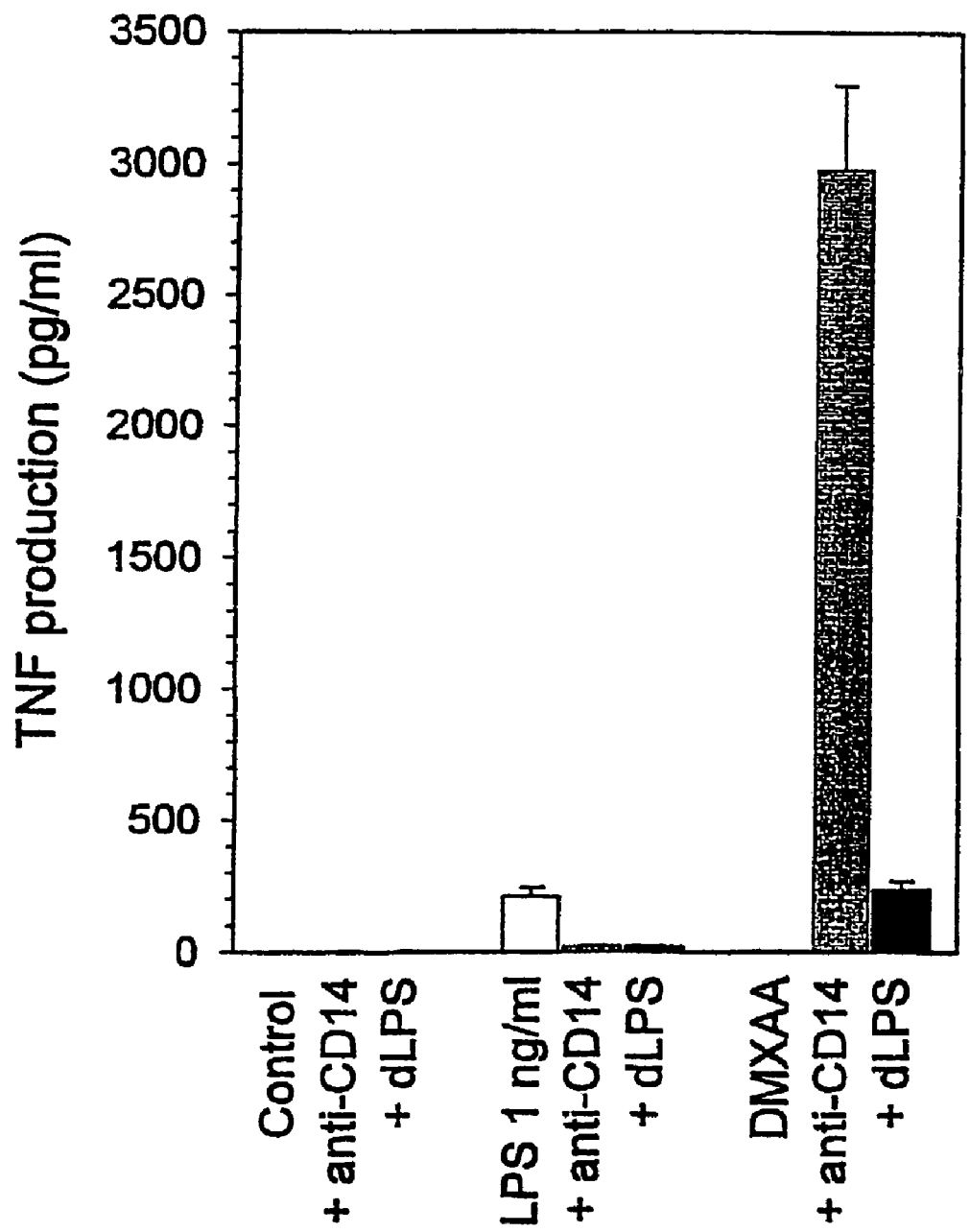
FIG. 7 shows the effect of anti-CD14 antibodies and dLPS on TNF production in response to LPS and DMXAA in murine leucocytes in vitro. Murine leucocytes were pre-incubated for 15 minutes with or without either an9-CD14 antibodies (10 μl/well) or dLPS (500 μg/ml) before the addition of DMXAA (800 μg/ml), DMXAA (800 μg/ml) or LPS (1 ng/ml). Cultures were incubated for 8 hours and the TNF content of the supernatant was measured.

As seen in FIG. 7, control cells, cells treated with anti-CD14 antibodies alone, or cells treated with dLPS alone produced very low concentrations of TNF. LPS significantly increased TNF production and this increase was abolished by coincubation with anti-CD14 antibody or dLPS. DMXAA alone did not significantly increase TNF production, but co-incubation with anti-CD14 antibody resulted in a high level of TNF production that was even greater than that caused by LPS. Coincubation with dLPS also caused a significant ($p<0.001$) elevation of TNF production, although the magnitude of the effect was less than that caused by anti-CD14 antibody.

Example 8

The possible role of LPS for the in vivo production of TNF in mice was reviewed by pre-treating mice with a combination of antibiotics designed to sterilise the gut. The results support the concept that DMXAA acts as a co-stimulator with other inducers of TNF in both murine and human mononuclear cells.

To test the hypothesis that low concentrations of LPS synergise with DMXAA for in vivo TNF production, mice were treated orally with antibiotics for 3 days and then treated with 25 mg/kg DMXAA. TNF levels were measured 24 hours later.

In Vivo Studies

C57BL mice were either untreated, or treated for 4 days prior to DMXAA with a mixture of antibiotics (cephalocin 2 g/l and neomycin 2 g/l in the drinking water). Mice received a single i.p. dose of DMXAA (25 mg/kg) and blood was collected by cardiac puncture of halothane-anaesthetised mice after 3 hours. Blood from each mouse was transferred to individual microcentrifuge tubes and allowed to clot overnight on ice before centrifugation at 2000×g for 20 minutes at 4° C. If clotting was not complete the sample was allowed to stand on ice for a further 2 hours, after which it was re-centrifuged. Serum was drawn off the top of the blood samples and stored at −20° C. until assay of TNF content.

Measurement of TNF

TNF standards were prepared by making serial dilutions of the TNF stock solution in supplemented culture media (concentration range 10-10,000 pg/ml). ELISA (enzyme-linked immunosorbent assay) plates were made using the OptEIA Human TNF-alpha-Set (Pharmingen, San Diego, Calif., USA). TNF standards and samples were added to the ELISA plates and the assays were carried out according to the manufacturer's directions.

Effect of Antibiotic Treatment

Figure 8:
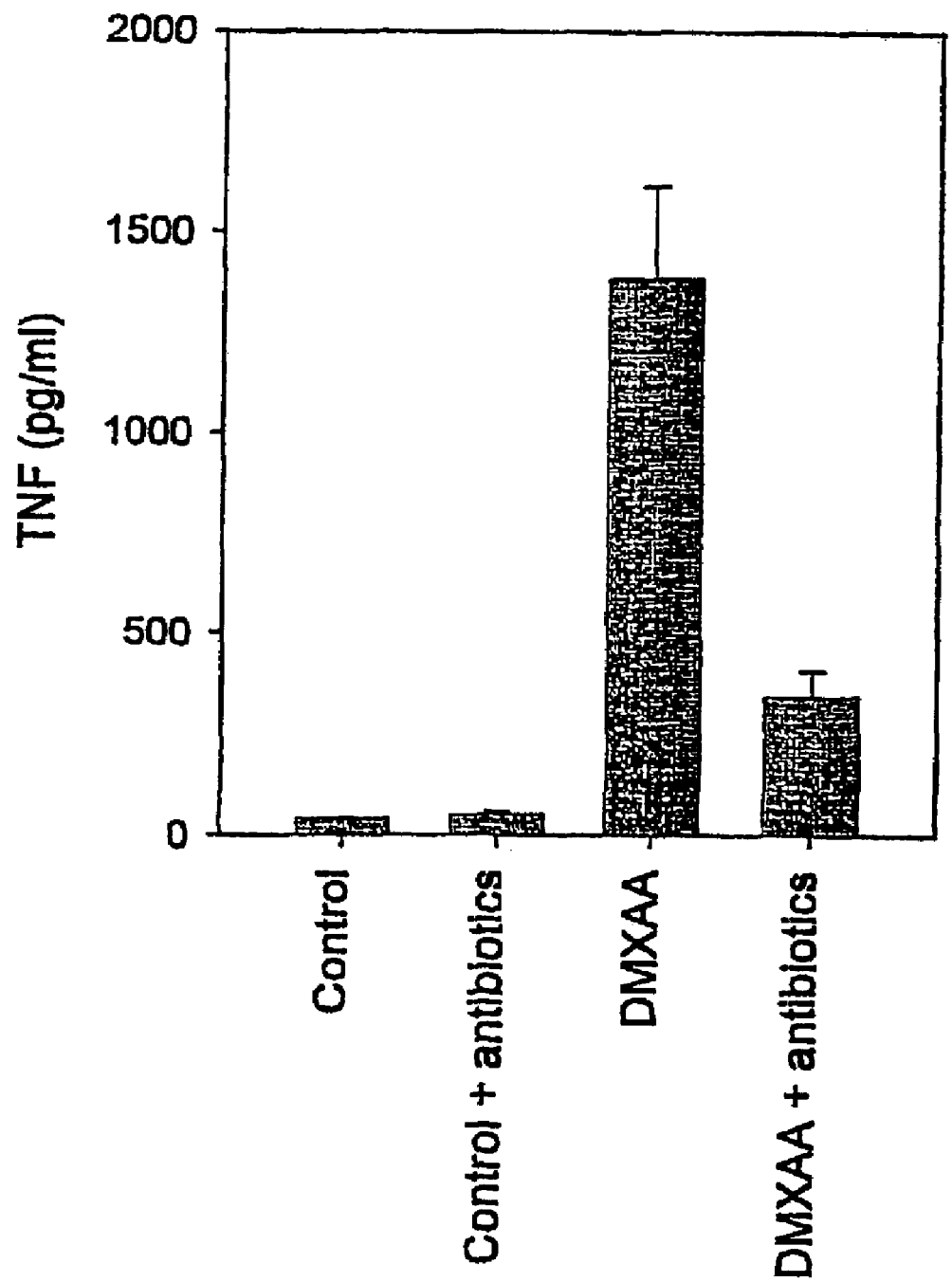
FIG. 8 shows the effect of antibiotic treatment on in vivo TNF production. Mice were treated orally for three days with an antibiotic combination to reduce the bacterial flora in the gut. Mice were then treated with DMXAA (25 mg/kg) and TNF was measured 24 hours later.

TNF concentrations were low in control mice and in mice treated with antibiotics alone. As shown in FIG. 8, treatment with DMXAA substantially increased serum TNF concentrations in mice not receiving antibiotics. Administration of DMXAA to mice following antibiotic treatment also increased serum TNF but the increase was significantly smaller ($p<0.001$) than that in mice not receiving antibiotic treatment.

Discussion

The results of the above Examples (1-8) show that DMXAA appears to require a second signal for the induction of TNF synthesis with human leucocytes, and also demonstrates a similar effect with murine leucocytes. It is notable and unexpected that anti-CD14 antibody and dLPS, which bind to the CD14 receptor for LPS and thus inhibit TNF induction by LPS, provide a signal that enables DMXAA to induce TNF (FIG. 7). The results of antibiotic pre-treatment (FIG. 8) strongly support the hypothesis that small amounts of circulating bacterial products, which could include LPS or LPS products, are required for the TNF response to DMXAA.

The results suggest that combination of DMXAA with a strategy for increasing the second signal in tumour tissue, such as by use of compounds capable of contributing to modulation of TNF synthesis, may lead to a combination therapy having significant clinical anti-tumour effect. The increased induction of TNF, and the resultant effect this will have on tumour growth, is a significant advance of considerable public interest.

INDUSTRIAL APPLICATION

As will be apparent from the above description and examples, the present invention provides an improved method of cancer therapy that is expected to find widespread clinical utility. The invention also provides compositions of use in such methods of cancer therapy.

Those persons skilled in the art will understand that the specific description provided thereof is exemplary only and that the present invention is not limited thereto. Alterations and modifications that would be apparent to a person skilled in the art are intended to be included within the spirit and scope of the invention as defined in the appended claims.

The invention is:

1. A method of treating cancer, the method including the step of administering to a mammal in need of such treatment, either simultaneously or sequentially:
   (i) 5,6-dimethylxanthenone-4-acetic acid having the formula

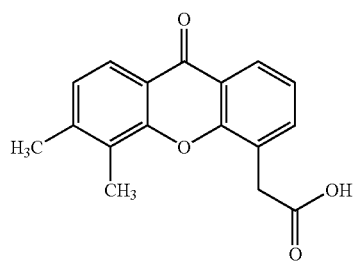

DMXAA or a pharmaceutically acceptable salt or ester thereof; and
   (ii) a compound selected from the group consisting of deacylated LPS and a CD-14 receptor antibody, wherein said administering results in TNF-α induction in excess of that induced by either agent alone.

2. A pharmaceutical composition suitable for treating cancer, including
   (i) 5,6-dimethylxanthenone-4-acetic acid having the formula

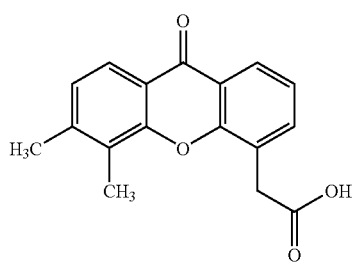

(DMXAA)

or a pharmaceutically acceptable salt or ester thereof, and
   (ii) a compound selected from the group consisting of deacylated LPS and a CD-14 receptor antibody, wherein the amounts of the compound of (i) and the compound of (ii) are selected to provide TNF-α induction in excess of that induced by either agent alone.

3. A method of preparing a medicament for treating cancer, comprising combining
   (i) 5,6-dimethylxanthenone-4-acetic acid having the formula

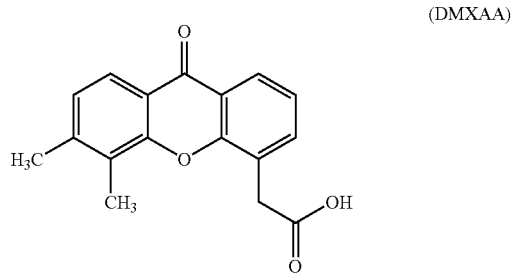

(DMXAA)

or a pharmaceutically acceptable salt or ester thereof, with
   (ii) a compound selected from the group consisting of deacylated LPS and a CD-14 receptor antibody,
   wherein the amounts of the compound of (i) and the compound of (ii) are selected to provide TNF-α induction in excess of that induced by either agent alone.

4. The method of claim 3, further comprising combining said 5,6dimethylxanthenone-4-acetic acid or pharmaceutically acceptable salt or ester thereof, and said compound selected from the group consisting of deacylated LPS and a CD-14 receptor antibody, with a pharmaceutically acceptable carrier.

5. A method of treating cancer, the method including the step of administering to a mammal in need of such treatment, either simultaneously or sequentially:
   (i) 5,6-dimethylxanthenone-4-acetic acid having the formula

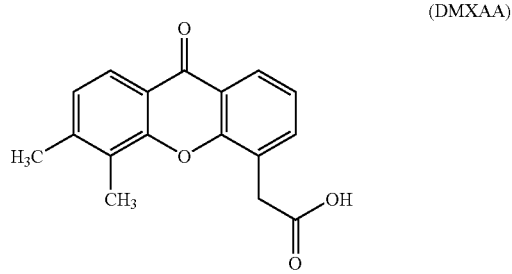

(DMXAA)

or a pharmaceutically acceptable salt or ester thereof; and
   (ii) a compound of deacylated LPS, wherein said administering results in TNF-α induction in excess of that induced by either a sent alone.

6. The method according to claim 1, wherein the compound of (ii) is a CD-14 receptor antibody.

7. A pharmaceutical composition suitable for treating cancer, including
   (i) 5,6-dimethylxanthenone-4-acetic acid having the formula

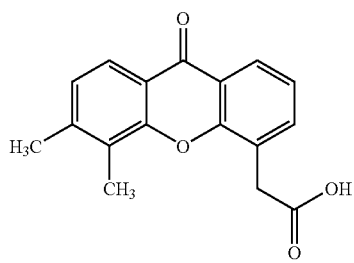

(DMXAA)

or a pharmaceutically acceptable salt or ester thereof, and
   (ii) a compound of deacylated LPS, wherein the amount of the compound of deacylated LPS is selected to provide TNF-α induction in excess of that induced by either agent alone.

8. The pharmaceutical composition according to claim 2, wherein the compound of (ii) is a CD-14 receptor antibody.

9. A method of preparing a medicament for treating cancer, comprising combining
   (i) 5,6-dimethylxanthenone-4-acetic acid having the formula

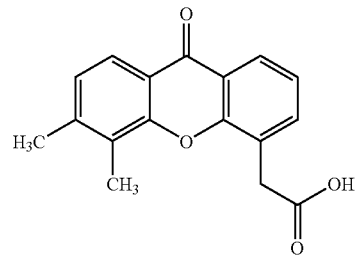

(DMXAA)

or a pharmaceutically acceptable salt or ester thereof, with
   (ii) a compound of deacylated LPS, wherein the amount of the compound of deacylated LPS is selected to provide TNF-α induction in excess of that induced by the compound of deacylated LPS alone.

10. The method according to claim 3, wherein the compound of (ii) is a CD-14 receptor antibody.

11. The method of claim 9, further comprising combining said 5,6-dimethylxanthenone-4-acetic acid or pharmaceutically acceptable salt or ester thereof, and said deacylated LPS, with a pharmaceutically acceptable carrier.

12. The method of claim 3, further comprising combining said 5,6dimethylxanthenone-4-acetic acid or pharmaceutically acceptable salt or ester thereof, and said CD-14 receptor antibody, with a pharmaceutically acceptable carrier.

* * * * *